(12) United States Patent
Wood (10) Patent No.: US 9,850,516 B2
(45) Date of Patent: Dec. 26, 2017

(54) SPORE DETECTOR

(71) Applicant: LOCKHEED MARTIN CORPORATION, Bethesda, MD (US)

(72) Inventor: John Arthur Wood, Bethlehem, PA (US)

(*) Notice: Subject to any disclaimer, the term of this patent is extended or adjusted under 35 U.S.C. 154(b) by 57 days.

(21) Appl. No.: 14/627,813

(22) Filed: Feb. 20, 2015

(65) Prior Publication Data
US 2015/0307913 A1    Oct. 29, 2015

Related U.S. Application Data

(60) Provisional application No. 61/942,969, filed on Feb. 21, 2014.

(51) Int. Cl.
*C12Q 1/04* (2006.01)
*G01N 21/64* (2006.01)

(52) U.S. Cl.
CPC .......... *C12Q 1/04* (2013.01); *G01N 21/6408* (2013.01); *G01N 21/6486* (2013.01); *G01N 2333/32* (2013.01)

(58) Field of Classification Search
None
See application file for complete search history.

(56) References Cited

U.S. PATENT DOCUMENTS

| | | | |
|---|---|---|---|
| 5,005,005 A | 4/1991 | Brossia et al. | |
| 5,474,910 A | 12/1995 | Alfano | |
| 6,838,292 B1 | 1/2005 | Rajan et al. | |
| 6,885,440 B2 | 4/2005 | Silcott et al. | |
| 7,106,442 B2 | 9/2006 | Silcott et al. | |
| 7,591,980 B2 | 9/2009 | Call et al. | |
| 2004/0014154 A1* | 1/2004 | Ponce | C12Q 1/04 435/7.32 |
| 2006/0238757 A1* | 10/2006 | Silcott | G01N 15/0618 356/338 |
| 2009/0095053 A1 | 4/2009 | Creek et al. | |

FOREIGN PATENT DOCUMENTS

WO    2013/172976    11/2013

OTHER PUBLICATIONS

3M, Information for Employers and Workers Concerned About Anthrax, Available Nov. 21, 2001, Online at: multimedia.3m.com/mws/media/259822O/ employers-and-workers-concerned-about-anthrax.pdf.*

(Continued)

*Primary Examiner* — Karen Cochrane Carlson
*Assistant Examiner* — Jennifer M. H. Tichy
(74) *Attorney, Agent, or Firm* — Oblon, McClelland, Maier & Neustadt, L.L.P.

(57) ABSTRACT

A system and method of detecting spores includes a light source configured to emit a light pulse within a first wavelength range, and a light sensor configured to detect a resulting phosphorescence emitted from one or more desiccated spores phosphorescing within a second wavelength range in a vicinity of the light pulse. The spore detector also includes circuitry configured to trigger emission of the light pulse and record the emitted phosphorescence at a predetermined time after the light pulse.

22 Claims, 8 Drawing Sheets

(56) References Cited

OTHER PUBLICATIONS

Lou Reinisch, et al., "Phosphorescence in Bacillus Spores," Department of Physics and Astronomy, University of Canterbury, Christchurch, New Zealand, Jul. 2003, 8 Pages.
SKC, Inc., "Determination of Fine Particulate Matter in Indoor Air Using Size-Specific Impaction," IP-10A Method Update, Publication No. 1660 Rev. 1008, 2004, 21 Pages.
Geddes, Chris D., "Ultra-fast and Ultra Sensitive Multiplexed Pathogen Detection," Baltimore, MD.
Ingram, Andrew J. et al., "Speciation, Luminescence, and Alkaline Flourescence Quenching of 4-(2-Methylbutyl) aminodipicolinic acid (H2MEBADPA)," J Phys Chem A., Jul. 14, 2011.

* cited by examiner

ANTHRAX PHOSPHORESCENCE SENSOR IN PERSONAL PARTICULATE SAMPLER

400

Perspective View

410

420

Exciter LED Flash

Light Sensor with Green Filter

Filter Element

430

Side Cut-Away View

Flashing via a light source, a light within a first wavelength range
S610

Initiating via circuitry, a light sensor, wherein the light sensor is gated for a pre-determined time from the flashing light and is filtered to record emitted phosphorescence within a second wavelength range
S620

Detecting via the light sensor, the emitted phosphorescence from desiccated spores within a vicinity of the flashing light at the

SPORE DETECTOR

CROSS-REFERENCE TO RELATED APPLICATION

This application claims the benefit of U.S. Provisional Application No. 61/942,969, filed on Feb. 21, 2014, the disclosure of which is incorporated in its entirety by reference herein.

BACKGROUND

There are several methods of collection and analysis of spores. In one method, the bare sides of a glass optical fiber are treated with a substance that adsorbs the target substance, causing a change in refractive index of the surface of the optical fiber. The change in refractive index changes how much light leaks out of the curved, treated segment, causing a change in signal received by the light receptor. However, any phosphorescent or fluorescent materials in contact with the sensor could distort readings by introducing a competing light source.

Another method uses fluorescence only to detect and identify a wide range of biological substances, and many biological substances other than spores fluoresce, potentially masking the presence of spores. The fluorescence is detectable only while the exciting light is on, and does not continue after the light is turned off.

One device for spore detection impacts the spores onto a reactive substrate on a filter wheel, and the substrate combines with certain portions of the spore to make phosphorescent products. The phosphorescent products allow the system to be very sensitive, detecting as few as 1000 spores in one spot. However, the device does not make use of the native phosphorescence of the spores.

Another device utilizes a Mie (Rayleigh) scattering and fluorescence of a continuous laser beam to identify each particle. Phosphorescence of the biological particle is not possible since the device does not view the particle after it leaves the point at which it is illuminated by the laser.

Another device measures multiple optical properties, including the refractive index and the size and fluorescence of each individual particle as it passes through the target zone. Each particle is identified from these properties. However, it does not use phosphorescence as a measurable characteristic.

Another method of spore detection concentrates spore particulates onto a spot prior to analysis. This is not a real-time method since the particulates need to be collected for a period of time, and the spot of particulates is rotated to the measurement device for a reading. Biological, chemical, and radiological properties of the particulates are identified.

Another method utilizes ultrafine fluorescent particles that are attached to target particles in the air stream. The attachment of the ultrafine particles to the target particles produces a change in the optical properties of the ultrafine fluorescent particles or the target particles, or both. The ultrafine particles are selected to be specific to a class of target particulates, such as biological particulates, or the ultrafine particles can be specific to a particular target particulate in cases of monitoring for the presence or absence of a single contaminant.

Another method utilizes a high intensity near-field light to form an optical trap to hold particles in place for a variety of optical and physical measurements. An interrogating light can be applied from an external light source to a trapped substance, in which small particles suspended in fluids move around randomly due to Brownian motion. However, a substance is subjected to a near-field optical trap for an extended period of time, and this method does not allow for measurement techniques in a dynamic system.

SUMMARY

Aspects of the disclosure include methods and systems for detection of desiccated spores. Phosphorescent properties of the desiccated spores are utilized for detection and identification.

Embodiments include a spore detector with a light source configured to emit a light pulse within a first wavelength range, and a light sensor configured to detect a resulting phosphorescence emitted from one or more desiccated spores phosphorescing within a second wavelength range in a vicinity of the light pulse. The spore detector also includes circuitry configured to trigger emission of the light pulse and record the emitted phosphorescence at a pre-determined time after the light pulse.

Embodiments include a method of detecting spores. The method includes flashing via a light source, a light within a first wavelength range, and initiating via circuitry, a light sensor. The light sensor is gated for a pre-determined time from the flashing light and is filtered to record emitted phosphorescence within a second wavelength range. The method also includes detecting via the light sensor, the emitted phosphorescence from desiccated spores within a vicinity of the flashing light at the pre-determined time.

Embodiments include a spore detector system. The spore detector system includes one or more spore detectors configured to detect a presence of desiccated spores within a defined vicinity. Each spore detector includes a light source configured to emit a light pulse within a first wavelength range, and a light sensor configured to detect a resulting phosphorescence emitted from the desiccated spores phosphorescing within a second wavelength range in a vicinity of the light pulse. Each spore detector also includes circuitry configured to trigger emission of the light pulse and record the emitted phosphorescence at a pre-determined time after the light pulse.

BRIEF DESCRIPTION OF THE DRAWINGS

Various exemplary embodiments will be described in detail with reference to the following figures, wherein.

The foregoing paragraphs have been provided by way of general introduction, and are not intended to limit the scope of the following claims. The described embodiments will be best understood by reference to the following detailed description taken in conjunction with the accompanying drawings.

DETAILED DESCRIPTION

The disclosure herein describes in part, a low cost real-time sensor for detecting desiccated *Bacillus* and other spores in HVAC systems. The sensor is used to monitor indoor biological threats, wherein the threat is located to the nearest HVAC zone.

Embodiments described herein provide a real-time signal when relatively large levels of spores enter the HVAC system and are in the process of being spread throughout the building. It can be used to trigger automated responses to limit the spread of the threat. Embodiments herein also describe a mobile spore-detecting unit that can be used in conjunction with a wearable mask or used as a standalone self-contained unit.

*Bacillus* and other spores, when dry (desiccated), exhibit phosphorescence when illuminated by ultraviolet light. The *Bacillus* spore, when illuminated by 270 nanometers (nm) light produces phosphorescence at a wavelength centered around about 500 nm (blue-green light). The inside of a HVAC duct is relatively dark, so optical sensors experience relatively little interference. An embodiment includes a sensor that incorporates a 270 nm light-emitting diode (LED) that is configured to flash at a regular interval, and a light sensor that is set to look for and detect the approximately 500 nm phosphorescence emitted by the desiccated spores at a time in the range of 1 to 100 milliseconds after the LED light flashes. Other types of desiccated biological spores, when illuminated by an ultraviolet (UV) light of a first wavelength, phosphoresce at a second wavelength. This phosphorescence can be detected to identify a particular type and amount of biological spore.

Phosphorescence is a specific type of photoluminescence related to, but different from fluorescence. Unlike fluorescence, a phosphorescent material does not immediately re-emit the radiation it absorbs, as the processes required to re-emit energy occur less often. The slower time of re-emission is associated with "forbidden" energy state transitions. Some "forbidden" transitions occur very slowly in certain materials and could take up to several hours to be re-emitted at a lower intensity from the original excitation.

Figure 1:
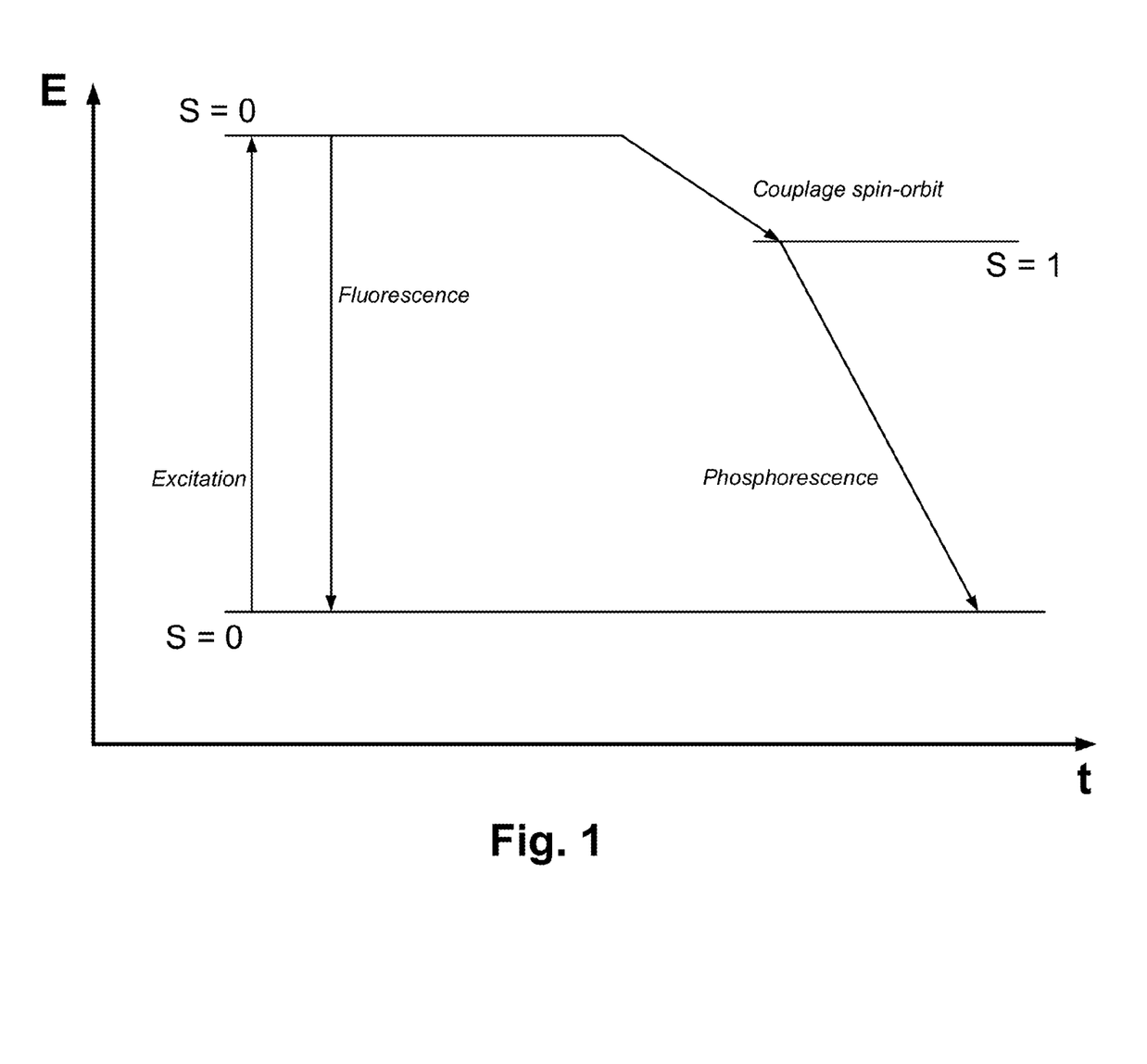
FIG. 1 illustrates fluorescence and phosphorescence according to one embodiment.

FIG. 1 illustrates a difference between fluorescence and phosphorescence in terms of energy, E over time, t. A material initially resides at a ground state, S=0. When the energy level of a material is excited, due to exposure from a UV flash of light for example, it's energy level increases to another ground state, S=0. The increased energy state is immediately released, via fluorescence and the material returns to its original unexcited state. Most photoluminescent events in which a material absorbs and re-emits a photon of light are fast, on the order of ten nanoseconds. Light is absorbed and emitted at these fast time scales in cases where the energy of the photons involved matches the available energy states and allowed transitions of the material.

In contrast, in the case of phosphorescence, the absorbed photon energy undergoes an unusual intersystem crossing into an energy state of higher spin multiplicity, usually a triplet state. As a result, the energy can become trapped in the triplet state with only classically "forbidden" transitions available to return to the lower energy state. These "forbidden" transitions still occur, but are kinetically unfavored, and thus progress at significantly slower time scales. When an electron absorbs a photon of high energy, it may undergo vibrational relaxations and intersystem crossing to another spin state. The system relaxes vibrationally in the new spin state and eventually emits light by phosphorescence. Most phosphorescent compounds are still relatively fast emitters, with triplet lifetimes on the order of milliseconds. However, some compounds have triplet lifetimes up to minutes or even hours, allowing these substances to effectively store light energy in the form of very slowly degrading excited electron states.

The phosphorescent properties of desiccated biological spores are used to advantage in embodiments described herein. Each individual or class of desiccated biological spores has a phosphorescent signature. When a particular desiccated biological spore is excited by a pulse of light at a given wavelength range, it will phosphoresce at another given wavelength range. For example, when a *Bacillus* spore is illuminated by a light pulse of approximately 270 nm, it produces phosphorescence at a wavelength centered around approximately 500 nm (blue-green light). Other desiccated biological spores will become activated to an excited state when exposed to their associated pulse light wavelength ranges, and subsequently phosphoresce at their respective phosphorescent wavelength ranges.

Phosphorescence requires the biological spores to be desiccated. The more desiccated the spores, the longer the phosphorescence. If a group of biological spores contains a certain amount of moisture, they will not phosphoresce. Spores phosphoresce because there is not enough water inside to allow for the collisional deactivation of the excited state before it can phosphoresce. All spores phosphoresce if they are sufficiently desiccated. Weaponized spores tend to be very desiccated. Extreme desiccation of weaponized spores increases the effectiveness of transporting the biological spores to a vast intended target. However, early identification of potential weaponized or damaging biological spores is possible using phosphorescent principles in systems and methods described herein.

A common vehicle in which biological spores are carried, including weaponized spores, is through a ventilation system, such as a heating, ventilation, and air conditioning (HVAC) system. The ventilation system pumps air throughout the system, which provides the mechanism by which desiccated spores can be delivered. The more desiccated the spores, the more effective the delivery. A spore identification system and method could be implemented within the ventilation system.

Figure 2:
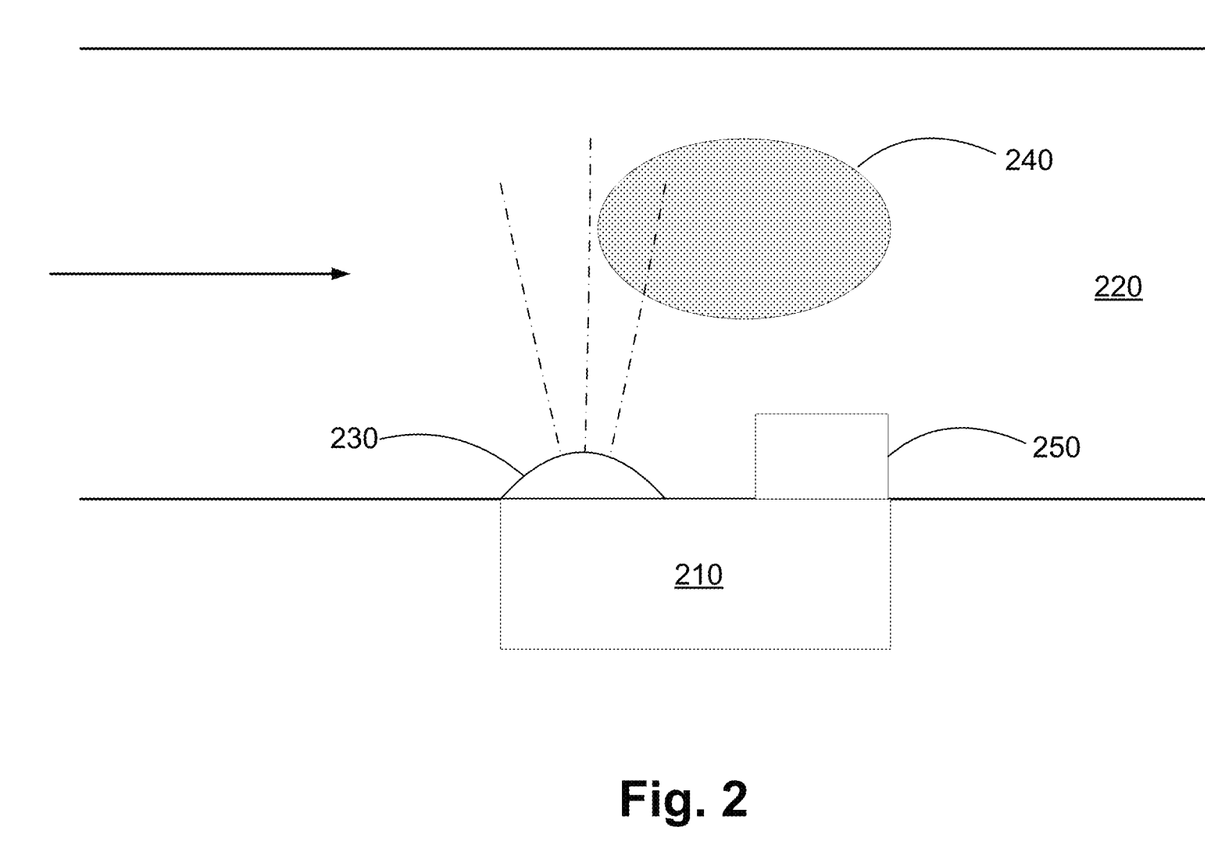
FIG. 2 illustrates a spore detector device according to one embodiment.

FIG. 2 illustrates a spore detector device 210 implemented within a ventilation duct 220. Air is flowing through the ventilation duct 220 in a direction from left to right within the page. The spore detector device 210 includes a UV light 230 configured to emit a light pulse when triggered by circuitry included in the spore detector device 210. A LED can be used since it has a long lifespan and uses minimal energy. However, other lights, such as a broad-band UV xenon flash lamp could also be used. When UV light 230 emits a light pulse at a particular wavelength, certain biological spores 240 within a vicinity of the UV light 230 can be activated into an excitation state. Shortly after excitation, the biological spores 240 emit phosphorescence, which is detected by a light sensor 250 at a pre-determined time after the light pulse from UV light 230 via the circuitry. In an embodiment for illustrative purposes only, a light pulse operating within a 270 nm range will irradiate *Bacillus* spores within the vicinity of the spore detector device 210. The light sensor 250 gated for detection at 1-100 milliseconds after the light flash can detect phosphorescence from the *Bacillus* spores within a 500 nm wavelength range. Other biological spores can also be detected by light sensor 250 when excited at their particular excitation wavelength ranges and emit phosphorescence at their respective phosphorescing wavelength ranges.

FIG. 2 illustrates the light sensor 250 located "down wind" with respect to the UV light 230. This orientation insures the biological spores 240 will be excited first and their subsequent phosphorescence will be detected by the light sensor 250 thereafter. The velocity of the ventilation air can be considered in determining the pre-determined time in which the light sensor 250 records phosphorescence subsequent to the light pulse from UV light 230. A faster ventilation air flow will result in a shorter pre-determined time in contrast to a slower ventilation air flow. Since the velocity of ventilation air flow is normally constant, an accurate pre-determined time can be easily established. However, the spore detector device 210 can be configured via the circuitry to automatically adjust to any variation in the ventilation air flow via a flow rate sensor.

The timing of the light pulse from the UV light 230 can be configured via the circuitry to flash on a regular timed basis. This would provide a substantially constant monitoring by the spore detector device 210 with minimal user intervention. In an embodiment, the UV light 230 could be configured by circuitry to flash or pulse for 0.1 milliseconds in duration every 100 milliseconds. However, other pulse durations and frequencies are contemplated by embodiments described herein. The results of the monitoring could be forwarded to a monitoring station, which could include measurement results from the light sensor 250. It could also include one or more displays within the vicinity of the spore detector device 210.

In another embodiment, results from the spore detector device 210 could be initiated by the presence of particulates in the vicinity of the spore detector device 210. However, the spore detector device 210 would also need to be configured to detect particulates in general, or have other sensing devices present that could initiate the spore detector device 210 when particulates are detected.

FIG. 2 illustrates one biological spore 240 for the sake of simplicity. However, several biological spores 240 would need to be present to detect a measurable amount of phosphorescence. Spore 240 could also be viewed as a spore cloud containing thousands or millions of individual spores. A measurable amount of biological spores 240 would depend on the anticipated amount of source material released and the dilution that is expected to take place before the biological spores 240 reach the light sensor 250. In an example given for Anthrax, one gram of material contains approximately 200 billion Anthrax spores. For calculation purposes, let us assume the material releases evenly into one cubic meter of space. By the time the spores are pulled into a duct and reach a sensor, they are diluted by a factor of 1000 to 10,000. Therefore, a sensitivity of about 10 million spores per cubic meter would probably be sufficient to detect an Anthrax spore delivery.

Other factors can improve conditions for a more successful spore detection at lower concentration levels. A more sensitive light sensor 250 could be used, the specifications of which would depend upon the needs of the building or structure where the ventilation system was located. Factors which could increase the detected sensitivity include increasing the intensity of the excitation of the UV light 230, using flat black paint on the inside of the ventilation duct 220, or using a measuring device to minimize the background of the ventilation duct 220. In addition, the lenses could be designed to focus more light onto the light sensor 250. Also, the electronic circuitry could sum the response of the light sensor 250 over a short period of time, such as one millisecond, rather than taking instantaneous readings.

In addition to confirming the presence of a particular biological spore, it is also desirable to measure the amount or density of the biological spores per unit volume of air. This can be estimated from determining the half-life of the biological spores. After emitting a light pulse from an excitation source, such as UV light 230, the phosphorescence is measured as it decays with time. To insure phosphorescence is being measured rather than fluorescence, the measurements need to occur when the UV light 230 is not emitting light. The intensity of detected phosphorescence is dependent on both the half-life and the number of spores. A single measurement at some specified time after the light pulse will not differentiate between a large concentration of spores with a short half-life and a smaller number of spores with a long half-life.

If all of the detected spores in the release have the same half-life, at least two measurements after each light pulse are necessary. If there is a mixture of spores with similar phosphorescent wavelengths but with different half-lives, at least three readings after the light pulse are needed to determine the two half-lives. In an embodiment, the light detectors 250 could be arranged to detect and record a phosphorescent measurement at different time intervals, wherein the later-spaced light sensors 250 allow the intensity to drop off enough to get a good determination of the percent change in intensity. For a HVAC system, the air flow carries the spores along the duct at a fairly high rate. Since the light sensors 250 are spaced downwind of the UV light 230, their locations and delay times could be determined from the duct air flow rate. In addition, dual UV lights 230 having different wavelengths could be utilized for further target discrimination. In an embodiment, the two UV lights 230 could flash alternately.

For additional sensitivity, linear arrays of light sensors 250 located downwind of a linear array of UV lights 230 could include cylindrical lenses placed above the linear arrays of light sensors 250 to focus more of the light onto the light sensors 250 in the air duct 220. If a diffraction grating is placed below the cylindrical lenses, different phosphorescent wavelengths could be separated onto slightly separated parallel rows of light sensors 250, which could respond to different types of biological spores 240.

Figure 3A:
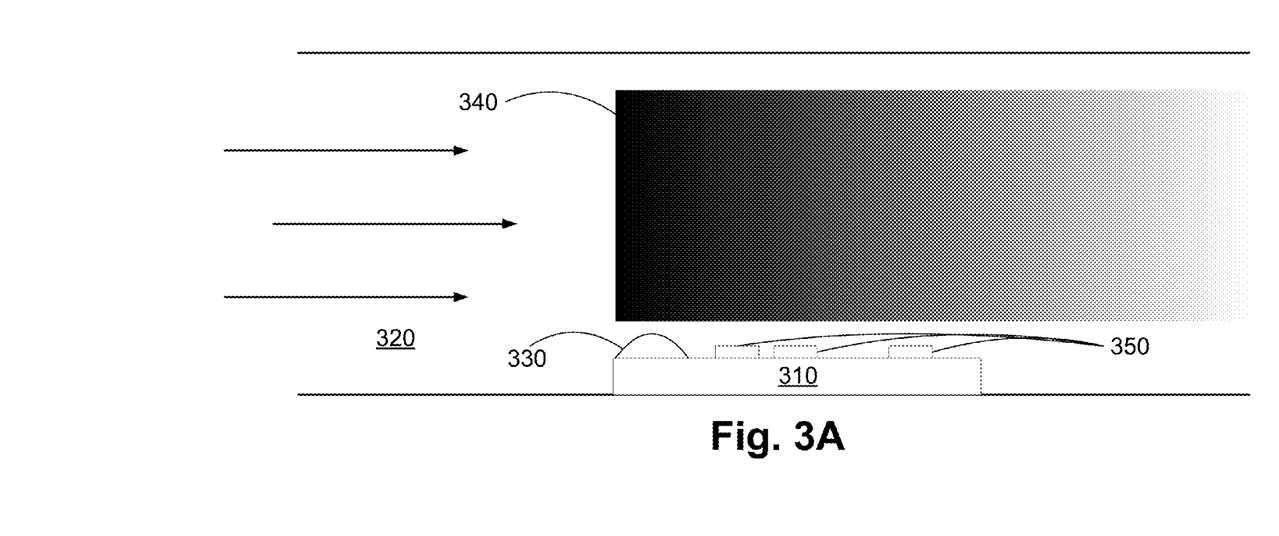
FIGS. 3A-3B illustrate detection of spores at one or more different wavelengths according to one embodiment.

FIG. 3A illustrates a spore detector 310 placed within a ventilation air duct 320. The spore detector 310 includes a UV light 330 configured to emit a timed light pulse via circuitry within the spore detector 310. The UV light 330 causes a wave of biological spores 340 in the vicinity to phosphoresce at one or more different wavelengths. The phosphorescence is measured by multiple light sensors 350, which are spaced apart on the spore detector 310. Measurements from the multiple light sensors 350 provide an estimate of the intensity and decay rate of the biological spores 340.

Phosphorescence and the selection or identity of biological spores 340 can be measured using different methods or systems. The biological spores 340 can be excited and identified by different wavelengths emitted by the UV light 330. Selection can also be made by different phosphorescence wavelengths that are identified using multiple light sensors 350. The intensity of phosphorescence is proportional to the concentration of biological spores and therefore, a sudden increase above background indicates a spore burst release.

Figure 3B:
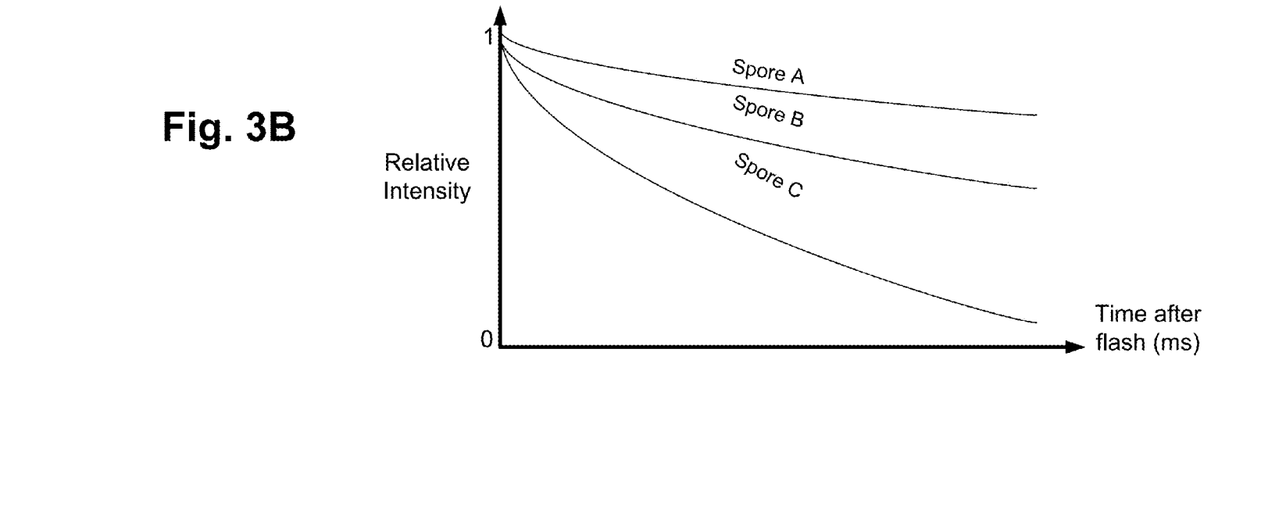

Selection can also be made by the decay rate. FIG. 3B illustrates phosphorescent decay among three different types of biological spores. The decay rate will likely differ among different types of biological spores and also among differing degrees of hydration. Weaponized spores are likely to be the most desiccated and therefore, have the longest phosphorescent half-life.

The embodiments described above were illustrated using a single spore detector device contained within an air duct of a ventilation system. However, most ventilation systems are divided into multiple zones, e.g. multiple HVAC zones. HVAC zones can be determined by branching, both in terms of construction needs and air handling capacity. The larger the building, the more HVAC zones present in the ventilation system.

In an example of a HVAC system, given for illustrative purposes only, a central feed can go up through the center of the building with one branch on each side for each floor. Therefore, two zones would be present for each floor or wing. If a building is very spread out, the number of zones can be determined by the architectural configuration. There may be auxiliary blowers in both the feed lines and the return lines. In other cases, zones can be defined as separately controlled temperature regions. In buildings with dual hot and cold ducts, each room can include a separate temperature-controlled branch of air flow.

Embodiments described herein include a spore detector system, wherein a spore detector device, such as spore detector device 210 or 310 is located within each ventilation zone of a ventilation system. The multiple spore detector devices are interconnected via circuitry and controlled by a computer processor, which can be located within the building or located remotely. In addition, the controller for the spore detector system can be programmed to respond to a particular type and/or level of biological spores detected. For example, the air flow within some or all of the air ducts of the ventilation system can be shut down or diverted when a dangerous type and/or amount of biological spore is detected. In addition, alarms can be programmed to sound, along with announcements for evacuation of the building, if necessary. The alerts can also be forwarded to local response units, as well as other branches of the affected entity.

Figure 4A:
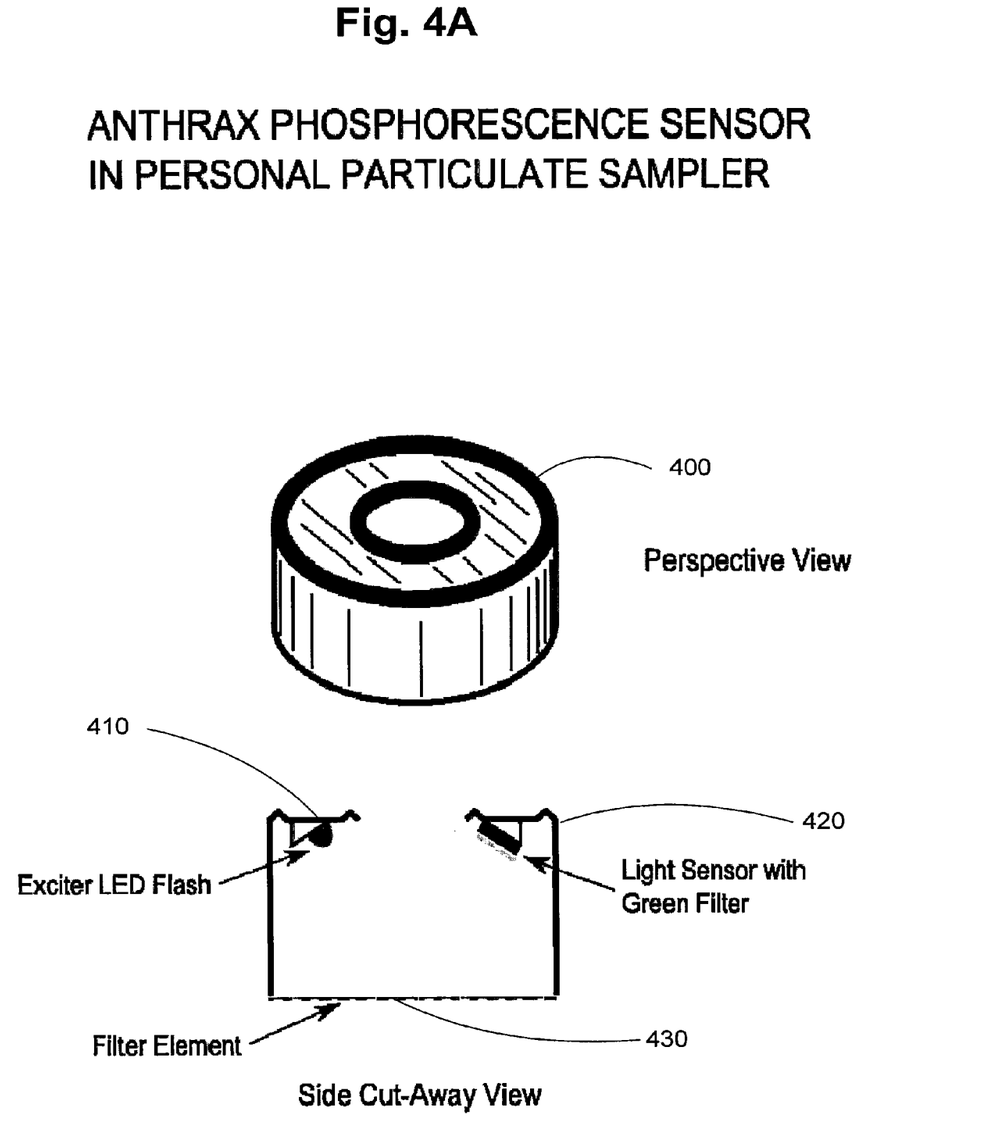
FIGS. 4A-4B illustrate an anthrax phosphorescence sensor within a personal particulate sampler according to one embodiment.

Embodiments herein also describe a spore detector device which can be a mobile standalone self-contained unit, or it can be configured to be combined with another type of mobile device. FIG. 4A illustrates a perspective view of an anthrax phosphorescence sensor 400 implemented within a personal particulate sampler. An excitation source 410, such as a LED configured to emit a light pulse or light flash is located in an upper corner of the sensor 400. A light sensor 420 faces the spores illuminated by the excitation source 410 within the unit of the personal particulate sampler. In the illustrated embodiment, the light sensor 420 is configured with a green filter. Light sensor 420 is timed by circuitry to read at set intervals after each flash of the excitation source 410. A filter element 430 is located at a bottom region of the sensor 400 for collecting air particulates.

Figure 4B:
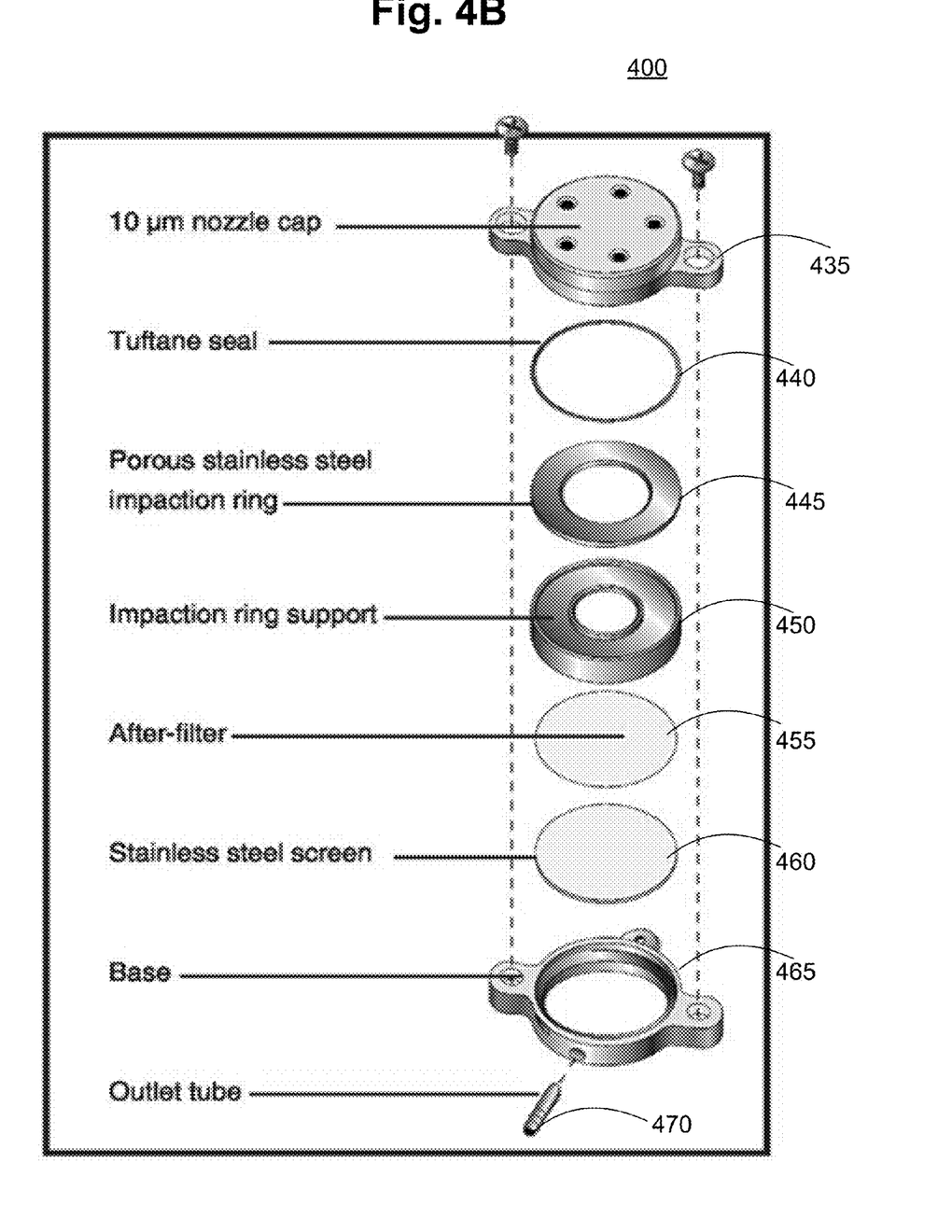

FIG. 4B illustrates a more detailed view of sensor 400. Sensor 400 includes a nozzle cap 435 with multiple nozzles through which air enters the sensor 400. A seal 440, such as a tuftane seal is located against the nozzle cap 435. Air is accelerated through the nozzles of the nozzle cap 435 and forced to impinge upon a porous impaction ring 445, such as a stainless steel impaction ring. Porous impaction ring 445 serves as an impaction surface and as a clamping ring for an after-filter. Air passes through the inlet nozzles of the nozzle cap 435 and impacts onto an annular disk of porous material cemented onto a ring that clamps the after-filter to a base. Smaller particles flow through the circular opening in the center of the impaction plate.

An impaction ring support 450 provides physical support to the impaction ring 445. An after-filter 455 provides a collection site for air particulates forced through the sensor 400. In an embodiment, particles larger than a designated cut-size impact onto the impaction ring 445 due to inertia. Smaller particles are carried along in the airstream and are collected within the after-filter 455. After-filter 455 can be configured to collect fine or coarse particulates at different flow rates. In addition, multiple impaction rings 445 can be included to collect different sized particles.

A support screen 460, such as a stainless steel screen supports the after-filter 455 and is located at the bottom side of the sensor 400. A base 465 is secured to the nozzle cap 435 by screws, which secures all intermediate elements together to form an airtight seal between the after-filter 455 and base 465. An exit plenum or outlet tube 470 provides an exit for the air forced through the sensor 400. The outlet tube 470 is connected by tubing to a pump to provide the filtering action.

The weight gain of the after-filter 455 and the total volume of air sampled can be measured to calculate particulate levels of a specific sized particulate matter. In an embodiment, the concentration of the particulate matter in a batch of sampled air can be expressed in micrograms per cubic meter, as $C=M_S/V_S$ where C is the concentration of particulate matter, $M_S$ is the mass of particulate matter found on the sample filter, and $V_S$ is the volume of sampled air.

Figure 5A:
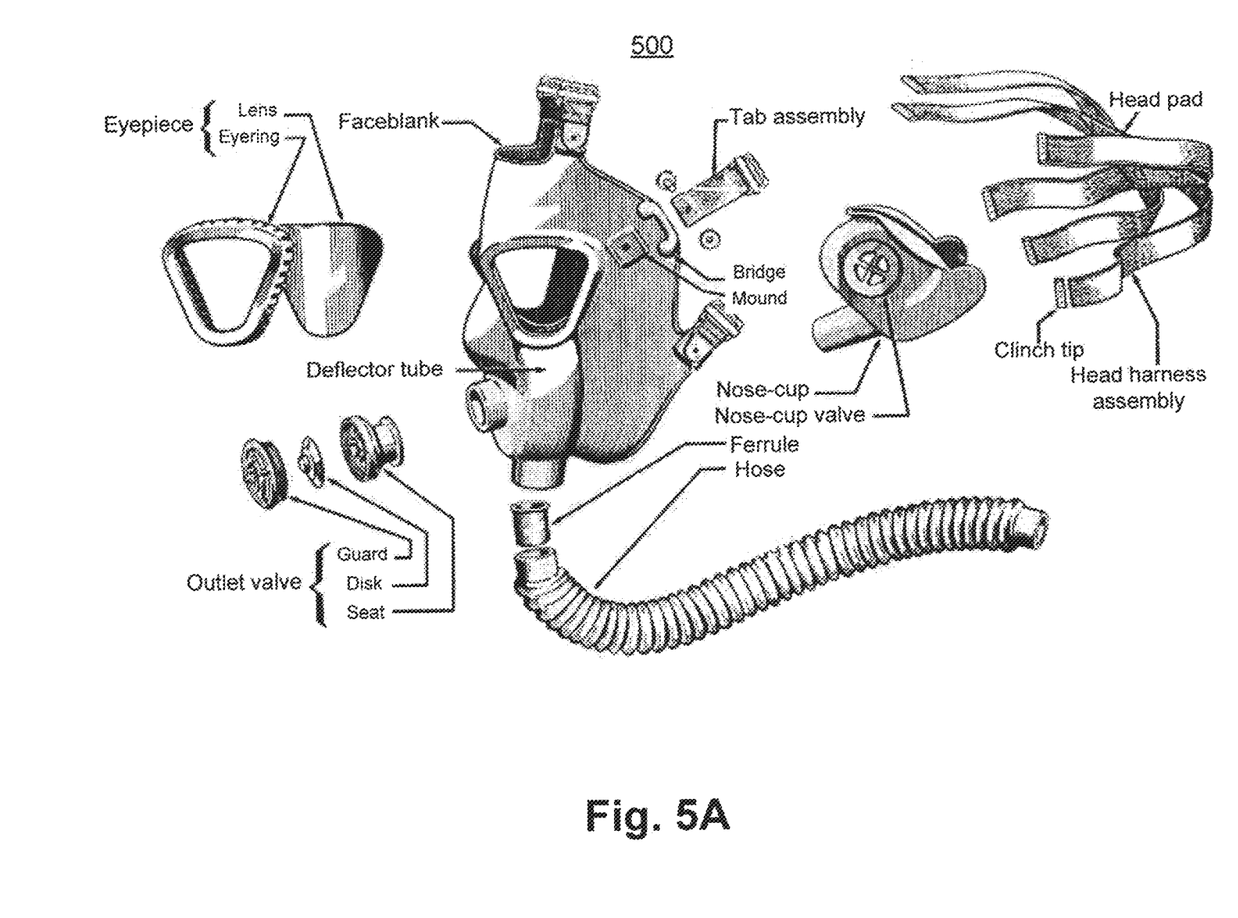
FIG. 5A illustrates a gas mask according to one embodiment.

In an embodiment, the spore detector device can be integrated into a ventilation mask that is worn by an individual to detect biological spores within the individual's environment. FIG. 5A is a schematic of an illustrative gas mask 500. However, most types of gas masks can be used in conjunction with embodiments described herein. Gas mask 500 is just one example of a gas mask that can be used with embodiments described herein.

Figure 5B:
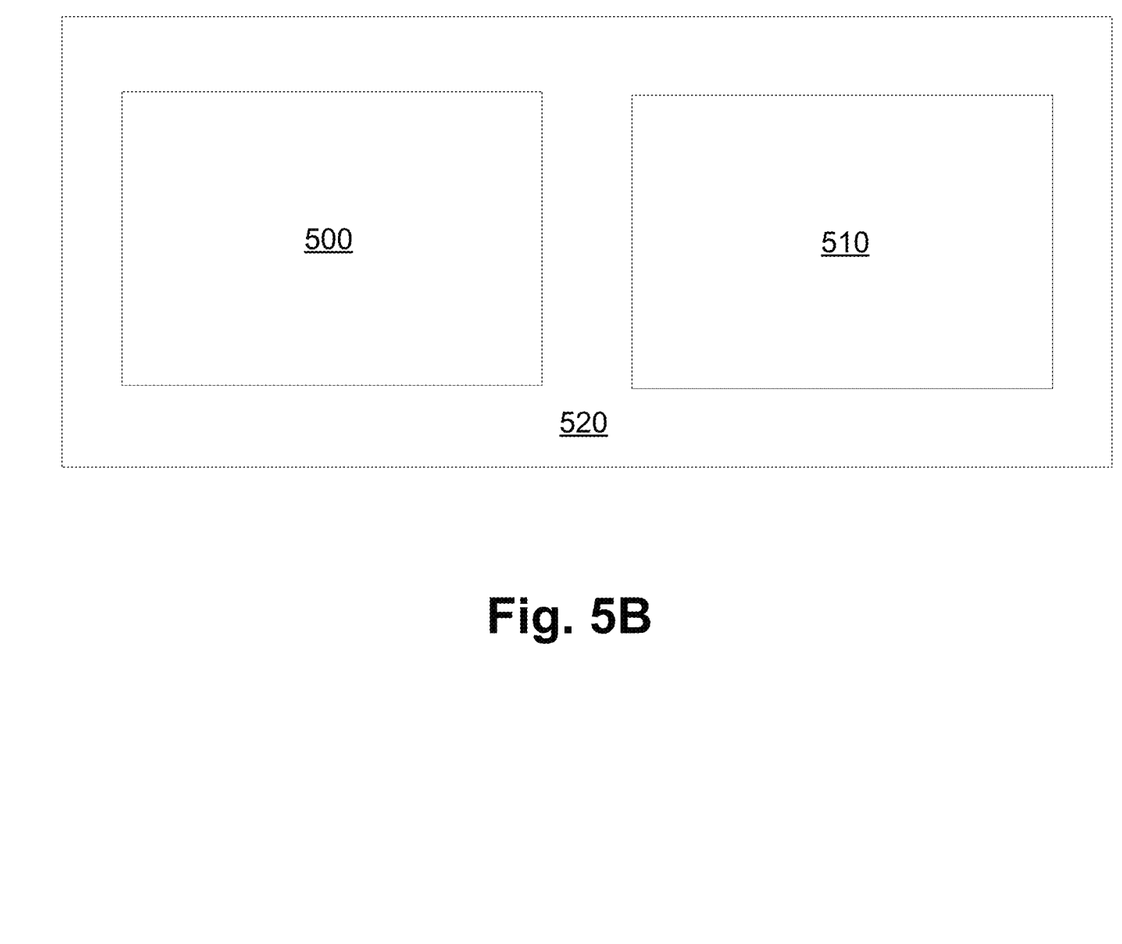
FIG. 5B is a block diagram illustrating a combined gas and spore detector according to one embodiment.

FIG. 5B is a block diagram illustrating a gas mask 500, such as the gas mask illustrated in FIG. 5A. Block 510 illustrates a particulate sampler, such as sensor 400 illustrated in FIGS. 4A-4B. Gas mask 500 and sensor 510 can be combined as a personal gas mask and spore detector 520. It can be worn as a single unit on the person and be used to detect gas and spores within the area.

Embodiments herein describe a spore detector that includes a light source configured to emit a light pulse within a first wavelength range, and a light sensor configured to detect a resulting phosphorescence emitted from one or more desiccated spores phosphorescing within a second wavelength range in a vicinity of the light pulse. The spore detector also includes circuitry configured to trigger emission of the light pulse and record the emitted phosphorescence at a pre-determined time after the light pulse.

The spore detector can have a first wavelength range of approximately 250-290 nm. The light sensor can be configured to detect the emitted phosphorescence at a second wavelength range centered about a 500 nm wavelength. The pre-determined time can be approximately 1-100 milliseconds. The light sensor can be configured to detect phosphorescing desiccated biological spores.

The spore detector can be configured to be mounted within a ventilation system, wherein the pre-determined time can be calibrated with respect to a velocity of air flowing through the ventilation system. The spore detector can also be configured as a mobile unit or configured in conjunction with a ventilation mask.

The light source can be configured to emit multiple light pulses at one or more wavelength ranges. The spore detector can also include a plurality of light sensors configured to detect a half-life of the one or more desiccated spores.

A spore detector system includes one or more spore detectors. The detector system can include multiple spore detectors positioned within associated zones of a ventilation system. The detector system can also include a self-contained mobile spore detector.

Figure 6:
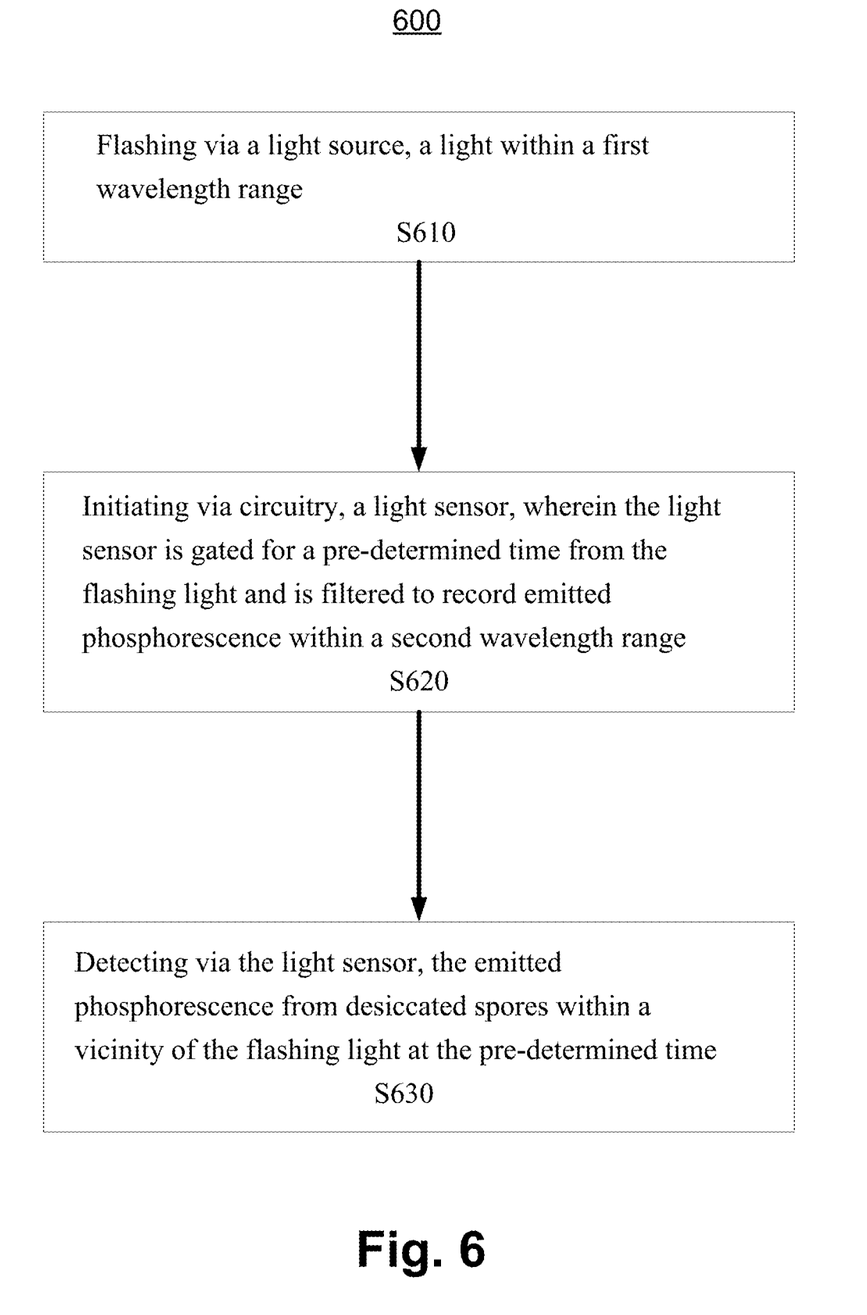
FIG. 6 is an exemplary flowchart for a method of detecting spores according to one embodiment.

FIG. 6 is an exemplary flowchart for a method 600 of detecting spores. Method 600 includes flashing via a light source, a light within a first wavelength range in step S610. A light sensor is initiated via circuitry in step S620, wherein the light sensor is gated for a pre-determined time from the flashing light and is filtered to record emitted phosphorescence within a second wavelength range. The emitted phosphorescence is detected via the light sensor in step S630 from desiccated spores within a vicinity of the flashing light at the pre-determined time.

Method 600 can also include sequentially flashing a plurality of lights via a plurality of associated light sources of varying wavelengths or wavelength ranges. In another embodiment, the light source can include multiple light emitters of varying wavelengths or wavelength ranges configured to flash simultaneously. Still another embodiment includes a broad-band flashing light source.

Method 600 can also include determining a half-life of the desiccated spores from results of the detected emitted phosphorescence, via multiple light sensors. Method 600 can also include distributing a plurality of spore detectors within established zones of a ventilation system, wherein each spore detector includes the light, the circuitry, and the light sensor. Method 600 can also include diverting or stopping air flow of the ventilation system upon detecting the emitted phosphorescence.

In method 600, the first wavelength range can be set at a range to initiate phosphorescence from the desiccated spores. In an embodiment for a ventilation system, the pre-determined time can be set at a time in which the desiccated spores will reach the light sensor, subsequent to the flashing. In a self-contained spore detector or a mask with a spore detector, the light sensor identifies the phosphorescence of desiccated spores within the illuminated area of the filter or the impaction plate, subsequent to flashing. The second wavelength range can be set at a range to capture the phosphorescence of a targeted spore type.

A hardware description of a computing device including one or more processors, databases, and/or servers used in conjunction with associated circuitry is included for embodiments described herein. The associated circuitry represents hardware and software components, whereby the circuitry elements of the embodiments noted above are programmed. This programming in hardware and software components constitutes algorithmic instructions to carry out the various functions and acts noted above. The computing device includes a controller processing unit (CPU) which performs the processes described above. The process data and instructions may be stored in a memory unit. These processes and instructions may also be stored on a storage medium disk such as a hard disc drive (HDD) or portable storage medium or may be stored remotely. Further, the claimed embodiments are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Embodiments described herein provide a real-time detection of spores within a vicinity using permanently installed or mobile spore detectors. A pulse of UV light excites desiccated spores within the vicinity and causes the spores to emit phosphorescence for some time after the light pulse has terminated, and which phosphorescence is measured at a pre-determined time or multiple predetermined times after the light pulse. The phosphorescence can be detected by one or more light sensors to determine the type and concentration of spores. This provides real-time detection for a real-time response and maximum containment of spores within a detection area.

While the invention has been described in conjunction with the specific exemplary embodiments thereof, it is evident that many alternatives, modifications, and variations will be apparent to those skilled in the art. Accordingly, exemplary embodiments as set forth herein are intended to be illustrative, not limiting. There are changes that can be made without departing from the spirit and scope of the invention.

The invention claimed is:

1. A spore detector, comprising:
   a light source in a first position configured to emit a light pulse within a first wavelength range;
   a light sensor in a second position a predetermined distance downwind from the light source, the light sensor configured to detect and record a resulting phosphorescence emitted from one or more moving desiccated spores phosphorescing within a second wavelength range in a vicinity of the light pulse while the one or more moving desiccated spores continue travelling downwind; and
   circuitry configured to trigger emission of the light pulse at the first position and record the emitted phosphorescence at the second position and at a pre-determined time after the light pulse;
   wherein the pre-determined time is calibrated with respect to a velocity of air flowing between the light source and the light sensor.

2. The spore detector of claim 1, wherein the first wavelength range is approximately 250-290 nanometers (nm).

3. The spore detector of claim 1, wherein the light sensor is configured to detect the emitted phosphorescence at the second wavelength range centered about a 500 nm wavelength.

4. The spore detector of claim 1, wherein the pre-determined time is approximately 1-100 milliseconds.

5. The spore detector of claim 1, wherein the light sensor is configured to detect phosphorescing desiccated biological spores.

6. The spore detector of claim 1, wherein the spore detector is configured to be mounted within a ventilation system.

7. The spore detector of claim 6, wherein the pre-determined time is calibrated with respect to a velocity of air flowing through the ventilation system.

8. The spore detector of claim 1, wherein the spore detector is configured as a mobile unit.

9. The spore detector of claim 8, wherein a mobile spore detector is configured in conjunction with a ventilation mask.

10. The spore detector of claim 1, further comprising: a plurality of light sensors configured to detect a half-life of the one or more desiccated spores.

11. The spore detector of claim 1, wherein the light source is configured to emit multiple light pulses at one or more wavelength ranges.

12. A method of detecting moving desiccated spores, the method comprising:
flashing via a light source in a first position, a light within a first wavelength range;
initiating via circuitry, a light sensor in a second position a predetermined distance downwind from the light source, wherein the light sensor is gated for a pre-determined time from the flashing light and is filtered to record emitted phosphorescence within a second wavelength range; and
detecting via the light sensor, the emitted phosphorescence from the moving desiccated spores within a vicinity of the flashing light at the pre-determined time while the moving desiccated spores continue travelling downwind;
wherein the pre-determined time is calibrated with respect to a velocity of air flowing between the light source and the light sensor.

13. The method of claim 12, further comprising: sequentially flashing a plurality of lights via a plurality of associated light sources of varying wavelengths or wavelength ranges.

14. The method of claim 12, wherein the light source includes multiple light emitters of varying wavelengths or wavelength ranges configured to flash simultaneously.

15. The method of claim 12, wherein the light source includes a broad-band flashing source.

16. The method of claim 12, further comprising: determining a half-life of the desiccated spores from results of the detected emitted phosphorescence, via multiple light sensors.

17. The method of claim 12, further comprising: distributing a plurality of spore detectors within established zones of a ventilation system, wherein each spore detector includes the light, the circuitry, and the light sensor.

18. The method of claim 17, further comprising: diverting or stopping air flow of the ventilation system upon detecting the emitted phosphorescence.

19. The method of claim 12, wherein the first wavelength range is set at a range to initiate phosphorescence from the desiccated spores, the pre-determined time is set at a time in which the desiccated spores will reach the light sensor subsequent to the flashing, and the second wavelength range is set at a range to capture the phosphorescence of a targeted spore type.

20. A spore detector system, comprising:
one or more spore detectors configured to detect a presence of moving desiccated spores within a defined vicinity, wherein each spore detector includes
a light source in a first position configured to emit a light pulse within a first wavelength range;
a light sensor in a second position a predetermined distance downwind from the light source, the light sensor configured to detect a resulting phosphorescence emitted from the moving desiccated spores phosphorescing within a second wavelength range in a vicinity of the light pulse while the desiccated spores continue travelling downwind; and
circuitry configured to trigger emission of the light pulse at the first position and record the emitted phosphorescence at the second position and at a pre-determined time after the light pulse;
wherein the pre-determined time is calibrated with respect to a velocity of air flowing between the light source and the light sensor.

21. The spore detector system of claim 20, wherein the spore detector system includes multiple spore detectors positioned within associated zones of a ventilation system.

22. The spore detector system of claim 20, wherein the spore detector system includes a self-contained mobile spore detector comprising the one or more spore detectors.

* * * * *